United States Patent
Baumann et al.

(10) Patent No.: US 7,398,309 B2
(45) Date of Patent: Jul. 8, 2008

(54) PROTON BEAM THERAPY CONTROL SYSTEM

(75) Inventors: Michael A. Baumann, Riverside, CA (US); Alexandre V. Beloussov, Bernardino, CA (US); Julide Bakir, Alta Loma, CA (US); Deganit Armon, Redlands, CA (US); Howard B. Olsen, Colton, CA (US); Dana Salem, Riverside, CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 665 days.

(21) Appl. No.: 10/433,817

(22) PCT Filed: Dec. 10, 2001

(86) PCT No.: PCT/US01/47634

§ 371 (c)(1),
(2), (4) Date: Nov. 28, 2003

(87) PCT Pub. No.: WO02/45793

PCT Pub. Date: Jun. 13, 2002

(65) Prior Publication Data

US 2004/0098445 A1 May 20, 2004

Related U.S. Application Data

(60) Provisional application No. 60/254,467, filed on Dec. 8, 2000.

(51) Int. Cl.
*G06F 15/173* (2006.01)
*A61N 5/00* (2006.01)

(52) U.S. Cl. .......................... 709/224; 250/505.1; 714/2

(58) Field of Classification Search .................. 709/201, 709/202, 224, 223; 702/188; 700/65; 250/492.1–492.3, 250/505.1, 492.23; 714/2, 30, 31, 44, 47, 714/48

See application file for complete search history.

(56) References Cited

U.S. PATENT DOCUMENTS

| 4,870,287 A | 9/1989 | Cole |
| 5,260,581 A * | 11/1993 | Lesyna et al. ............ 250/492.3 |
| 5,446,548 A | 8/1995 | Gerig et al. |
| 5,895,926 A | 4/1999 | Britton et al. |

(Continued)

OTHER PUBLICATIONS

Pyarali, I. et al. "Design and Performance of an Object-Oriented Framework for High-Speed Electronic Medical Imaging", Computing Systems, Usenix Association, Berkeley, CA, US vol. 9, No. 4, 1996, pp. 331-375.

(Continued)

*Primary Examiner*—Saleh Najjar
*Assistant Examiner*—David Lazaro
(74) *Attorney, Agent, or Firm*—Knobbe, Martens, Olson & Bear, LLP

(57) ABSTRACT

A tiered communications architecture for managing network traffic in a distributed system. Communication between client or control computers and a plurality of hardware devices is administered by agent and monitor devices whose activities are coordinated to reduce the number of open channels or sockets. The communications architecture also improves the transparency and scalability of the distributed system by reducing network mapping dependence. The architecture is desirably implemented in a proton beam therapy system to provide flexible security policies which improve patent safety and facilitate system maintenance and development.

92 Claims, 8 Drawing Sheets

PROTON BEAM THERAPY SYSTEM

U.S. PATENT DOCUMENTS

| | | | |
|---|---|---|---|
| 6,052,435 | A | 4/2000 | Hernandez-Guerra et al. |
| 6,085,227 | A | 7/2000 | Edlund et al. |
| 6,144,993 | A | 11/2000 | Fukunaga et al. |
| 6,505,245 | B1 * | 1/2003 | North et al. .................. 709/223 |
| 6,600,164 | B1 * | 7/2003 | Badura et al. ............ 250/492.3 |

OTHER PUBLICATIONS

Katehakis, et al. "A Distributed, Agent-Based Architecture for the Acquisition, Management, Archiving and Display of Real-Time Monitoring Data in the Intensive Care Unit", Foundation for Research and Technology, Hellas, Institute of Computer Science, Technical Report [Online] No. 261, Oct. 1999 URL:http//www.ics.forth.gr/{katehaki/publications/tr261.pdf>.

Kalet et al. "Designing radiotherapy software components and systems that will work together" Seminars in Radiation Oncology, Saunders, Philadelphia, PA, US vol. 7, No. 1, Jan. 1997 pp. 11-20.

Supplemental European Search Report for related PCT application PCT/US0147634, no date.

* cited by examiner

PROTON BEAM THERAPY SYSTEM

PROTON BEAM THERAPY CONTROL SYSTEM

RELATED APPLICATIONS

This application is the U.S. National Phase of PCT/US01/47634 /00065 filed Dec. 1, 2001 and claims priority to U.S. Provisional Application No. 60/254,467 Filed Dec. 8, 2000, which are hereby incorporated by in their entirety by reference herein.

This invention was made with Government support under grant DE-FG03-98ER62632 awarded by the Department of Energy. The Government has certain rights to this invention.

BACKGROUND OF THE INVENTION

1. Field of the Invention

The present invention relates to distributed control systems and, in particular, concerns a control system for managing data communications in a distributed environment for a proton beam therapy device.

2. Description of the Related Art

Radiation particle therapy devices are commonly used to treat localized forms of cancer as well as other afflictions. These devices are used to target specific regions of a patient, e.g. a tumor, and direct a precisely aligned stream of atomic particles or electromagnetic radiation towards the target region. The energy from the stream results in localized cell damage and effectively disrupts the growth and progression of the tumor.

One particularly useful form of radiation therapy is proton beam therapy wherein protons form the energy stream used to irradiate the target regions of the patient. Like other types of beam directed radiation therapy, proton beam therapy requires the patient to be accurately positioned with respect to the beam source so that the proton stream irradiates only the desired target region. Otherwise, the stream could damage other healthy cells within the patient's body.

As described in detail in U.S. Pat. No. 4,905,267 a support apparatus is used to position the patient with a particular orientation and the support apparatus is further positioned on a treatment platform within a gantry structure of the proton treatment facility. The proton treatment facility may further comprise more than one such treatment apparatus for the purposes of accommodating multiple patients. Control and monitoring of the apparatus and components of the treatment facility are directed by computer and hardware subsystems which coordinate the activities of each treatment station. In addition to the mechanical apparatus used to position the patient, proton beam therapy requires numerous other systems and software components which are used to control beam intensity, modify beam position, perform digital imaging, monitor safety conditions, and other functions. Together these systems form a complex and distributed collection of hardware and software components. Additionally, in a proton treatment facility with more than one treatment apparatus, the complexity of the system is further increased by the additional requirements for system redundancy and selective control of each treatment apparatus.

The complex architecture of distributed systems such as radiation therapy devices present numerous obstacles in allowing for coordinated control by a single application and further create networking difficulties between the components of the system. One particular limitation of conventional distributed systems relates to the management of data communications between the various components of the distributed system which becomes more difficult as the size of the distributed system increases. This problem is particularly apparent when a radiation therapy device is designed to contain more than one treatment apparatus. As a result, providing a centralized control and monitoring solution becomes a cumbersome task due in part to the number of communications channels which must be maintained. Additionally, the complex communications mapping schema presents difficulties in insuring that all devices can communicate with one another. Oftentimes, modifying or upgrading a single component of the distributed system necessarily results in the need to modify the configuration for a large number of other components to which the modified component was connected. Improper modification of the configuration for these components can result in numerous problems including loss of system control, inaccurate system monitoring, and device failure.

In a radiation therapy device, significant reconfiguration of the existing mapping schema in the aforementioned manner is undesirable as it introduces potential control issues which must be resolved in order to insure patient safety. If these issues are not properly resolved or if there is unexpected loss of control of one of more of the components during operation of the radiation therapy device, patient injury may occur. Therefore it is desirable to increase the level of transparency between components within the radiation therapy device to make the system more tolerant to modification and component upgrades.

FIG. 1 illustrates a conventional distributed system 40 comprising a plurality of hardware devices 50 each of which perform selected operations and tasks. Control and maintenance of the hardware devices 50 is coordinated using one or more host applications or processes 60 which communicate with the hardware devices 50 through a plurality of communication channels or data paths 70. For each hardware device 50 that the host application or process 60 communicates, a separate communications channel 70 is typically established.

A number of difficulties arise when using this approach which limit the coordination and management capabilities of complex distributed systems such as radiation therapy devices. In particular, when a large number of hardware devices 50 are to be managed or monitored by the host applications or processes 60, the required number of communication channels 70 that must be established and maintained becomes increasingly large. In many instances this results in increased system overhead necessary to manage the communication channels 70 which may grow to a point where the maximum number of communication channels 70 supported by the operating system or hardware components is exceeded. Thus, conventional distributed systems 40 provide limited scalability due to restrictions in the number of communications channels 70 which can be accommodated. Additionally, as the complexity of the distributed system 40 increases it becomes more difficult to perform effective network monitoring and authentication as well as maintain secure firewall policies to insure adequate system security.

A further problem arises in complex distributed systems 40 to insure that individuals who work with the architecture of the existing system 40 understand the communications mapping of the channels 70 and services within the system 40. This is especially important for developers who must have specific knowledge of how the hardware devices 50 are interconnected in order to add new hardware components or functionality. Conventional approaches insufficiently address this problem and rely on esoteric mapping schemes which may be difficult to understand and develop around.

Conventional distributed environments are typically based on a client/server paradigm. The client/server approach uses one or more monolithic host applications to poll individual systems of the distributed environment and piece the information together as needed. This method of information distribution and coordination is undesirable for a number of reasons, including the above-described maintenance difficulties, lack of scalability, and increased complexity in data verification and validation.

Additionally, in the proton beam therapy system there are numerous safety features which typically require constant monitoring of the underlying hardware devices and subsystems to operate. A conventional approach to this monitoring requirement is to have hardware monitoring take place exclusively at a host application level by a controlling program or application. One potential drawback using this approach is that a failure of the host application or the controlling program may result in a potentially unsafe or hardware-damaging condition. In some instances a "watchdog" program is employed to detect lapses in communication between the host application and the monitored hardware however the use of a watchdog program may have undesirable effects on the system.

In the case of a power supply, the watchdog program may automatically shut off the power supply to thereby invoke a system safe. This may result in the cooling of the power supply and subsequently result in a lengthy warm up period before patient treatment can resume. Furthermore, a failure in the proton beam therapy system may be masked until just prior to treatment, possibly delaying the treatment and adding to the discomfort of the patient.

Hence, there is a need for an improved system and methods for managing communications within complex and loosely coupled distributed environments such as that used in a proton beam therapy device. This system architecture should be able to accommodate the complexity and bandwidth demands of the proton beam therapy system while maintaining an acceptable level of simplicity so as to facilitate scaling, maintenance, and development. Additionally, the system should provide improved system monitoring features that resolve potential problems associated with monitoring off-line or malfunctioning devices.

SUMMARY OF THE INVENTION

The present invention comprises a tiered communications system for command, management and monitoring of a proton beam therapy system. In one aspect, the architecture of the proton beam therapy system includes one or more host applications or programs which communicate with hardware and/or resources used in patient treatment through an agent module. The agent transparently manages communications traffic and performs a number of administrative functions including data routing between the components of the proton beam therapy system. The communications system contains a monitor module which provides low level communications control and command translation for the various hardware devices and resources associated with the proton beam therapy system.

Communications coordination and management complexity is significantly reduced using the tiered communications system. In one aspect, the communications system architecture reduces channel or socket utilization by multiple processes using a routing/multiplexing functionality of the agent to resolve potential bottlenecks encountered coordinating data exchange between the hardware devices. The communications system further provides a constant monitoring capability for embedded systems using a proctor module.

A centralized connection architecture provides a further benefit of increased connection security which is important in maintaining the safety of patients treated using the proton beam therapy system. The communications system architecture additionally simplifies user interfacing and reduces the complexity of application development and deployment. For example, host applications can be configured to manage, monitor, and control embedded hardware devices without specific knowledge of the functional implementation or definitions required to communicate with each device. Additionally, the host applications can be configured to communicate with the embedded hardware devices without knowing the physical location of the device or its controlling system. In one aspect, logical mapping of this nature permits the flexible placement of devices within the system without substantial modification to the system configuration.

In one aspect the invention comprises a communications system for managing communications in a proton beam therapy device, wherein the system comprises a treatment station, one or more host applications, one or more functional components, and an agent. The treatment station is used to direct a calibrated and aligned beam towards a patient isocenter and the one or more host applications are used to monitor and control the operation of the treatment station through the functional components comprising hardware subsystems associated with the operation of the treatment station. The agent is connected to each host application and uses a single client data channel per host application. The agent is further connected to each functional component by a monitor data channel wherein the agent performs routing operations between each host application and the functional components such that each host application can communicate with each functional component using the single client data channel.

In another aspect the invention comprises a tiered communication architecture for a proton beam therapy device comprising a distributed network which operates using a reduced channel set and provides substantially transparent communications between one or more host applications and a plurality of hardware devices associated with the generation and alignment of a radiation beam used to treat a patient. The architecture further comprises an agent device connected to each application and to each hardware device by a plurality of discrete data channels wherein the agent routes communications between the one or more host applications and the plurality of hardware devices through the discrete data channels. The architecture further comprises a monitor component associated with each hardware device used to receive instructions from the host application routed through the agent and transform the instructions into a hardware recognized form that are subsequently executed on the hardware device, the monitor component further used to receive an information response from the hardware device and forward the information response back to the host application through agent. The architecture also incorporates a proctor component resident in the monitor component which evaluates the information response obtained from the hardware device and identifies anomalous hardware behavior and further issues one or more safety measures when anomalous hardware behavior is detected.

In yet another aspect the invention comprises a tiered communications system for managing communications in a distributed network. The system further comprises a client connected to the distributed network and configured to transmit instructions to a plurality of hardware devices through a single channel. Additionally, the system comprises an agent connected to the client through the distributed network and further connected to the plurality of hardware devices such that each hardware device is connected to the agent by a single channel wherein the agent receives the instructions transmitted by the client, identifies a destination hardware device for which the instruction is intended, and routes the instruction to the destination hardware device through an appropriate channel. The system further comprises a monitor associated with the destination hardware device and further connected to the distributed network which receives the instruction routed by the agent, identifies a hardware-recognizable command associated with the instruction, and thereafter issues the hardware-recognizable command to the destination hardware device for subsequent execution.

In still another aspect the invention comprises a method for exchanging information between a client and a plurality of hardware devices wherein the client issues instructions which control and monitor the plurality of hardware devices. The method further comprises the steps of: (1) establishing a first communication channel between the client and an agent which is configured to communicate with the client and receive instructions transmitted therefrom, (2) establishing a plurality of second communication channels between the agent and each hardware device, (3) routing the instructions issued by the client using the agent such that the instructions are forwarded to the appropriate hardware device in a substantially transparent manner, and (4) receiving the instructions using a monitor module residing on the hardware device which transforms the instructions into a hardware recognized format to be subsequently executed by the hardware device.

In yet another aspect, the invention comprises a method for exchanging information in a proton beam therapy system wherein at least one host application and a plurality of hardware devices are interconnected such that the at least one host application is desirably used to control and monitor the plurality of hardware devices through the transmission of a plurality of instructions. This method further comprises the steps of: (1) establishing a first communication channel between each host application and an agent device which is configured to communicate with the host application and receive the transmitted instructions, (2) establishing a plurality of second communication channels between the agent device and each hardware device such that each hardware device is connected to the agent by a single communication channel, (3) routing the instructions issued by the host applications using the agent device such that the instructions are forwarded to the appropriate hardware device in a substantially transparent manner, and (4) receiving the instructions using a monitor module residing on each hardware device which transforms the instructions into a hardware recognized format to be subsequently executed by the hardware device.

In still another aspect, the invention comprises a method for communicating and controlling a distributed system of network resources wherein a first communication channel is established between a client device and an agent device, a second communication channel is established between the agent device and at least one hardware device, and data transferred between the client device and the agent device and furthermore the agent device and the monitor device is processed according to a client process which requests access to the distributed system of hardware resources, an agent process which manages the communication channels and provides routing for client process requests, and a monitor process which accepts requests from the agent process, executes the requests, and returns any results to the client process.

BRIEF DESCRIPTION OF THE DRAWINGS

These and other aspects, advantages, and novel features of the invention will become apparent upon reading the following detailed description and upon reference to the accompanying drawings. In the drawings, same elements have the same reference numerals in which.

DETAILED DESCRIPTION OF THE PREFERRED EMBODIMENT

Figure 2:
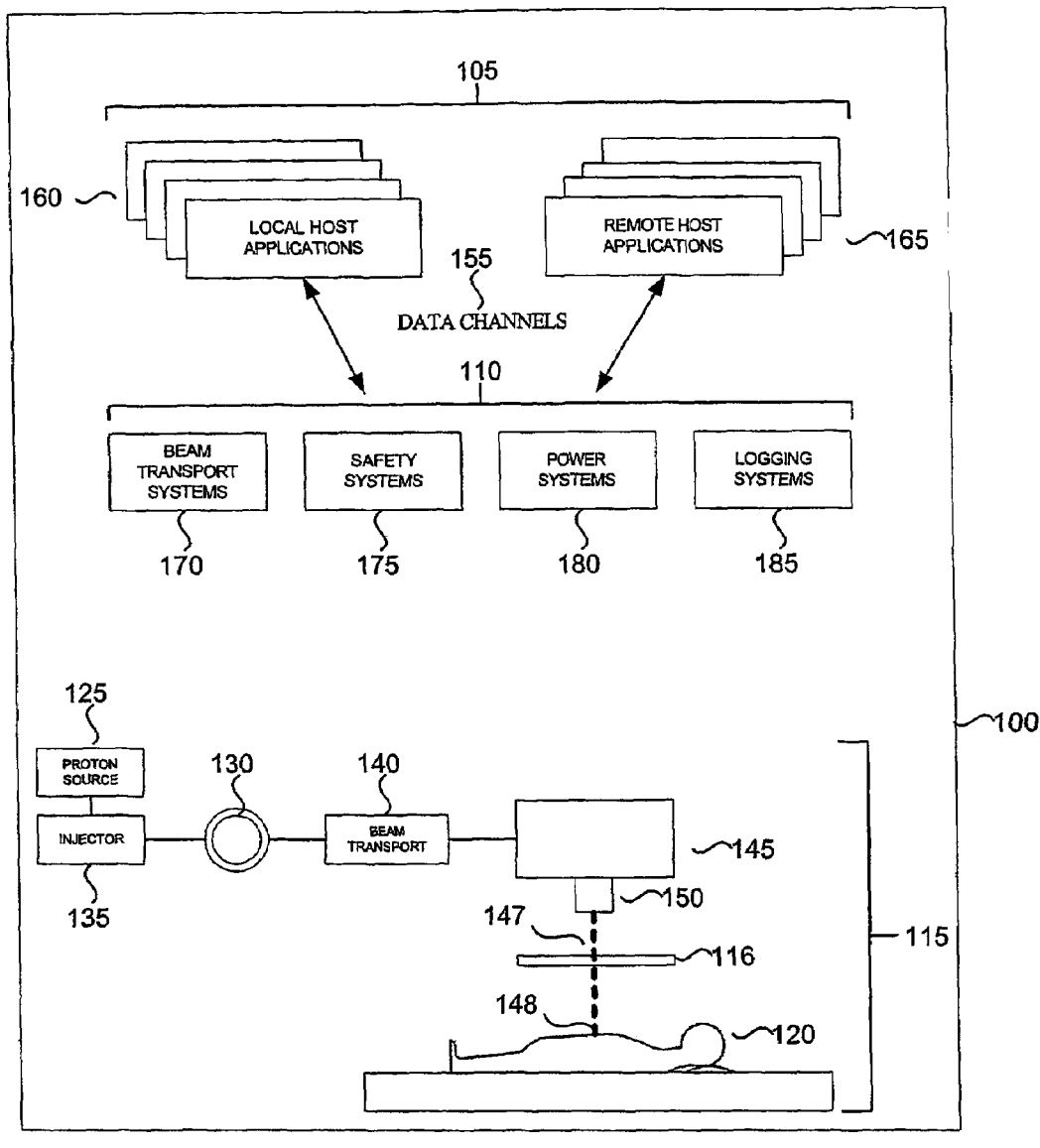
FIG. 2 illustrates one embodiment of a proton beam therapy system.

FIG. 2 illustrates one embodiment of a proton beam therapy system (PBTS) 100 for patient treatment that is coupled to one or more host applications 105. In one aspect, the host applications 105 communicate with a plurality of functional components 110 used in conjunction with a treatment station 115. The functional components 110 comprise monitoring and management components that direct the activities of the treatment station 115. Each functional component 110 further comprises one or more hardware devices present in the treatment station 115 which are desirably associated and collectively managed within the particle beam therapy system 100.

During the treatment process, the operation of these hardware devices are desirably coordinated to direct a precisely calibrated and aligned proton beam 147 towards a specific target region or isocenter 148 of the patient 120. In one embodiment, the treatment station 115 comprises a proton source 125 connected to an accelerator 130 by an injector 135. The accelerator 130 accelerates protons to a desired energy level and, via a beam transport apparatus 140, delivers the proton beam to the patient 120 who is supported in a fixed position at a treatment station 115. The beam transport apparatus 140 further comprises a nozzle 150 which directs the particle stream towards a specific target isocenter within the body of the patient 120. The patient 120 is supported by a gantry 145 which is rotatable about an axis of rotation and is used to properly align the proton beam. Additional details of the proton beam therapy system 100 can be found in commonly assigned U.S. Pat. Nos. 5,866,912 and 4,870,287 which are hereby incorporated by reference.

In aspect, the proton beam therapy system 100 comprises a plurality of treatment stations 115. Each treatment station 115 may be configured to share at least some of the same components such as the aforementioned proton source 125, accelerator 130, and injector 135. In one aspect, components which are shared between treatment stations 115 are monitored and controlled through a common control interface. Additional details of a proton beam therapy system which incorporates multiple treatment stations is described in U.S. Pat. Nos. 5,585,642 and 4,870,287 which are hereby incorporated by reference.

As is understood in the art of radiation therapy, it is important to deliver the proton beam or radiation stream accurately to the target isocenter. Further, proton beam or radiation stream therapy may be enhanced when the beam can be delivered from a variety of different angles. Hence, it is generally desirable to place the patient 120 in a fixed position relative to the nozzle 150 of the beam delivery apparatus 140 and to move the nozzle 150 of the beam delivery apparatus 140 to various positions via the movable gantry 145 such that the beam is delivered from a variety of different angles. U.S. Pat. Nos. 4,905,267 and 5,117,829 each disclose a system for aligning a patient 120 for radiation treatment and each of these references are hereby incorporated by reference. Furthermore, U.S. Pat. Nos. 4,917,344 and 5,039,057 each disclose a gantry system which allows for delivery of the beam over a continuous range of different angles and each of these patents are also hereby incorporated herein by reference. Various other methods of selecting treatment for patients, apparatuses for enhancing the delivery of particle or radiation beams to patients, and the like, are disclosed in U.S. Pat. Nos. 5,017,789, 5,240,218, 5,825,845, 4,905,267, 5,117,829 and 5,260,581 which are also hereby incorporated herein by reference.

The functional components 110 monitor and coordinate the activities of the hardware subsystems used to configure and direct the proton beam as well as insure patient safety. Patient safety is a primary concern in radiation treatment and strict control over the proton beam therapy system must be maintained at all times to insure that the beam is always directed with an appropriate intensity or energy level. In one embodiment, the beam therapy system is configured in such a manner so as to prevent the beam from contacting the patient unless the hardware devices and subsystems can be confirmed to be in a ready condition and appropriately configured. The ready condition indicates that the hardware devices and subsystems are performing within tolerances and at the specific range determined to be suitable for patient treatment. Typically, the proton beam is disabled until all subsystems can be confirmed to be in this ready condition. As will be described in greater detail herein below, the configuration of the functional components 110 and tiered communications system provides necessary coordination functionality to monitor the state of readiness of the proton beam therapy device to determine when it is appropriate to administer patient treatment.

In one aspect, the host applications 105 exchange information with the functional components 110 and provide the primary command and monitoring functionality for the radiation therapy system Host application 105 communication with the functional components 110 proceeds through a plurality of data channels 155 typically formed using conventional networking topologies. The host applications 105 and the functional components 110 are linked by the tiered communication network which utilizes a reduced number of data channels 155 compared to conventional systems to perform the data communications necessary to operate the proton beam therapy system 100.

The host applications may comprise both local host applications 160 and remote host applications 165. Local host applications 160 comprise applications run on computers or components directly associated with the proton beam therapy system 100. For example, the local host applications 160 may be run directly from computers associated with one or more of the hardware devices of the radiation therapy system 100. Alternatively, the local host applications 160 may be run from one or more standalone computers linked via networking connections to the hardware devices or subsystems of the radiation therapy system 100. Data exchange between the local host applications 160 and the one or more functional components 110 from which it receives and sends information proceeds through the aforementioned tiered communication network.

Remote host applications 165 comprise applications that are run externally and/or independently from the proton beam therapy system 100. In one aspect, remote host applications 165 are configured to interface with the proton beam therapy system 100 through the use of a remote networking protocol and need not be locally executed from the computers or components directly associated with the radiation therapy system 100. Like local host applications 160, remote host applications 165 utilize the tiered communication network to exchange data and information with the functional components 110 as needed or desired.

The functional components 110 comprise numerous subsystems associated with the operation of the proton beam therapy system 100. In one aspect, these subsystems 110 form a distributed network of computers and hardware devices which exchange data and information between one another and the host applications 105. As shown in FIG. 2, exemplary functional components 10 are shown for the purposes of illustration. These functional components include beam a transport system 170, a safety system 175, a power system 180, and a logging system 185.

It will be appreciated that radiation therapy systems are complex collections of interconnected devices and components which may include the aforementioned exemplary functional components 110 as well as numerous other components, systems and processes. Together these devices and subsystems form the distributed environment for which the tiered communication system of the present invention may be implemented to reduce channel complexity and improve patient safety.

In one aspect, the distributed environment of the radiation therapy system 100 includes a plurality of treatment stations 115 and associated hardware and software components useful for accommodating more than one patient at a time. The present invention is particularly suitable for adaptation to managing communications in a multi-station treatment facility where the complexity of the distributed environment is substantially increased over that of a single station treatment facility.

Although the tiered communications system is disclosed in the context of command, control, and monitoring of a proton beam therapy system 100 it will be appreciated that the invention may be adapted for use with other types of distributed systems to improve communications efficiency and reduce channel number. These alternative distributed system architectures are therefore understood to represent but other embodiments of the present invention as adapted for use with the system and methods described herein.

Figure 3:
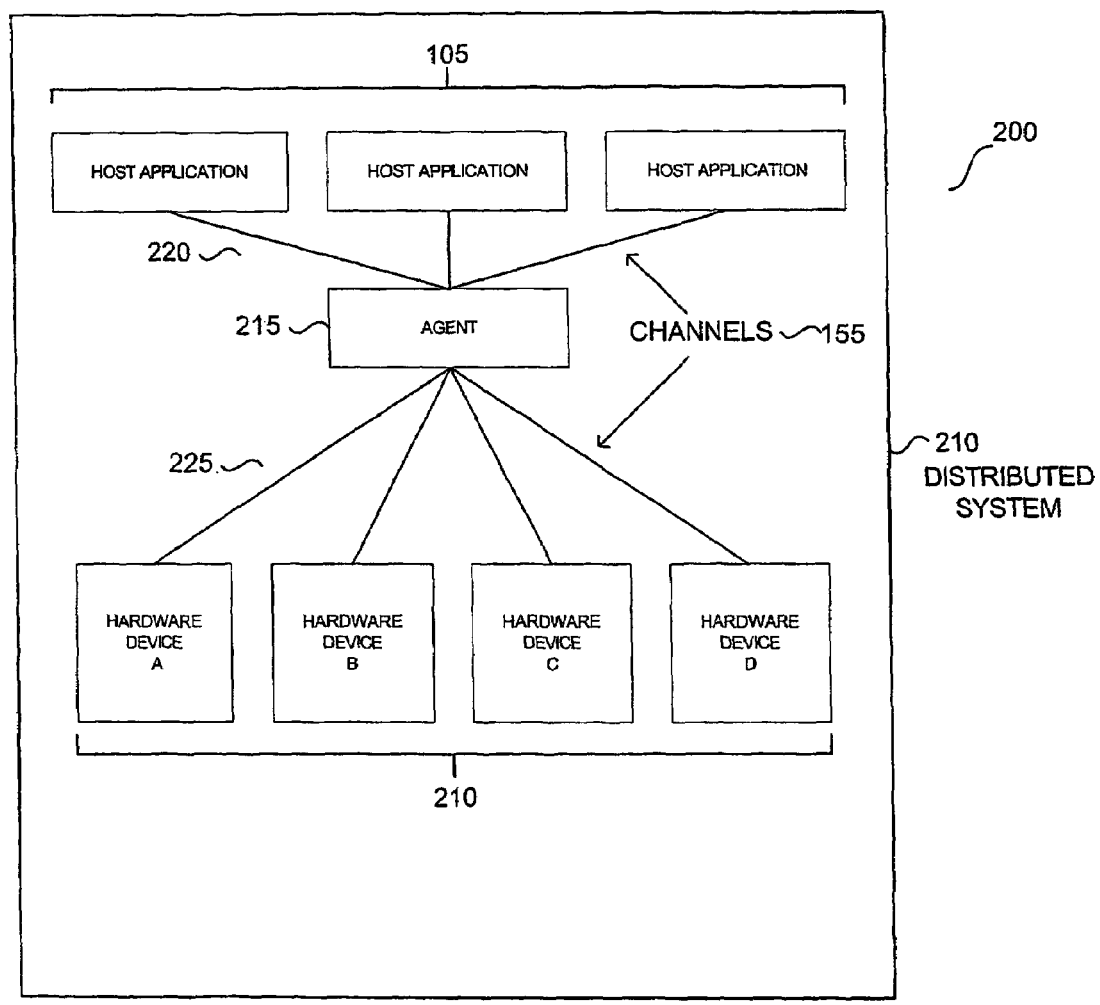
FIG. 3 illustrates one embodiment of the top level organization for a tiered communication system to be used in a distributed environment.

FIG. 3 illustrates a block diagram of the top level organization for a tiered communication architecture 200 for managing information exchange in a distributed environment such as the aforementioned proton beam therapy system 100. As previously indicated, the distributed system may comprise any of a plurality of hardware devices 210 including specialized controllers, computers, and other components which are desirably interconnected by networking connections to allow for communication and data exchange between the various devices 210. The tiered communication architecture 200 is implemented using a coordinated hardware and software-based approach wherein the hardware devices 210 are connected to the host applications 105 through a reduced set of data channels 155. Each host application 105 is interconnected with an agent device 215 such that a plurality of first data connections or data channels 220 is maintained between the host applications 105 and the agent device 215. The agent device 215 is further interconnected with each hardware device 210 of the distributed system 100 by a plurality of second data connections or data channels 225.

The connectivity between the host applications 105 and the agent device 215 as well as the agent device 215 and the hardware devices 210 comprises a networking connection which uses a suitable protocol such as Berkley sockets based Transmission Control Protocol, Internet Protocol (TCP/IP) or User Datagram Protocol, Internet Protocol (UDP/IP). The widespread interoperability of the sockets-based protocol may be advantageously used in the tiered communications system to provide a commonly-recognized communications protocol which each hardware device 210 is capable of using to transmit and receive information. Additionally, the sockets-based protocol possesses a number of advantageous properties including: (1) a generally well understood specification that developers may use for creating hardware interfaces, (2) reliable transmission and reception characteristics, (3) multithread compatibility, (4) support for multiple concurrent connections, and (5) support for blocking and non-blocking configurations. As will be described in greater detail herein below these properties are useful in simplifying the tasks associated with development of the tiered communications architecture 200 and may be configured for use with most hosts applications 105 and hardware devices 210 alike.

It will be appreciated by those of skill in the art that the tiered communications architecture 200 is not necessarily limited for use with the aforementioned sockets-based protocol but rather may be adapted for use with numerous other communications protocols including for example remote message passing protocols. The implementation of other protocols with the tiered communications architecture 200 is therefore understood to be representative of other embodiments of the present invention.

Figure 1:
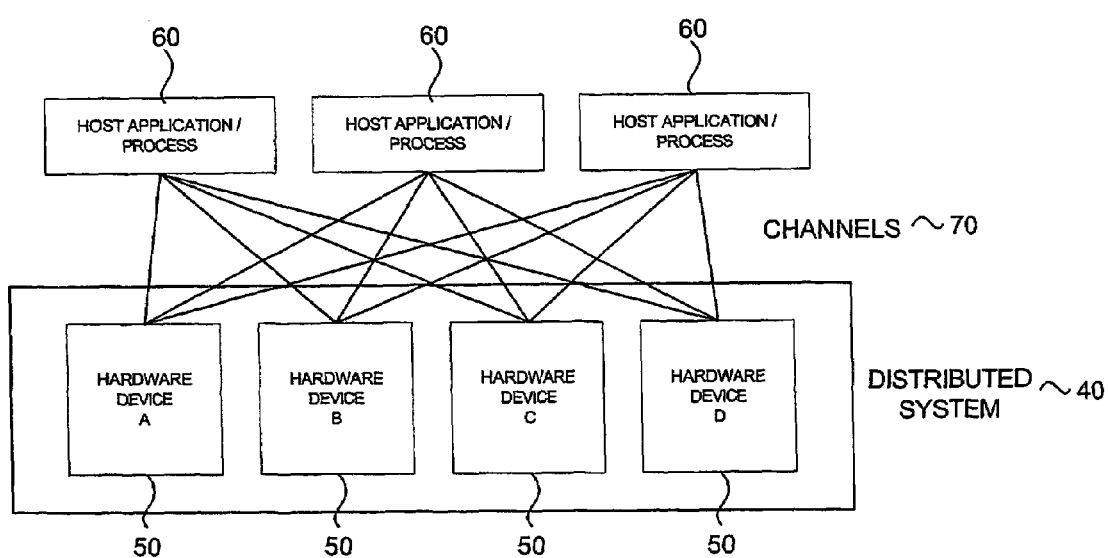
FIG. 1 illustrates a block diagram for a conventional distributed system.

As previously discussed in connection with FIG. 1, conventional distributed systems 40 must maintain a plurality of channels 70 between each host application 60 and the corresponding hardware devices 50. Thus, the total number of channels 70 required by conventional distributed systems grows rapidly which reduces performance and may exceed the design threshold of the architecture. The tiered communication architecture 200 overcomes this limitation and significantly reduces the total number of channels required for communication and data exchange in a distributed system such as the proton beam therapy device 100. For example, in the exemplified conventional distributed system 40, three host applications 60 are configured to communicate with four hardware devices 50 requiring a total of twelve channels 70. In comparison, as shown in FIG. 3 using the tiered communications architecture 200 to provide connectivity for the same number of host applications and hardware devices requires only seven channels.

It will be appreciated that the illustrated distributed system is but one embodiment of the present invention and other sizes/configurations of distributed systems will likewise benefit from reduced channel number when implementing using the tiered communication architecture 200. Additionally, the tiered communication architecture 200 may advantageously be configured for use with existing distributed systems permitting these systems to be retrofitted with this new communications architecture and benefit from reduced channel number and complexity.

A further benefit of the aforementioned distributed system configuration is that the host applications 105 can be configured to communicate with the hardware devices 210 without knowing the physical location of each device 110, its controlling system, or the agent 215. Logical mapping of this nature permits the flexible placement of components within the distributed system without substantial modification to the system configuration. In one aspect, the distributed system configuration of the present invention may be desirably applied to a proton beam therapy device to increase the scalability and flexibility of the system by substantially reducing mapping dependence between the system components. This feature is particularly useful in a proton beam therapy system which includes a multi-station treatment facility due to the fact that the system is more readily maintained and upgraded without requiring substantial reconfiguration when existing components are replaced or new components added to the system.

An important feature of the distributed system configuration relates to the computational complexity of adding a new host application 105 to the system. Conventional systems, such as that shown in FIG. 1, have a computational complexity of (N) for each host application to be connected to the hardware devices (where N is the number of hardware devices 50 in the distributed system 40). Additional host applications 60 each require N more channels 70 to be appropriately connected to the hardware devices 50. Thus for each additional host application 60, the number of channels 70 increase as the function (M*N) where M represents the number of host applications present in the distributed system.

In the present invention the computational complexity and cost of host application addition is substantially reduced over that of the prior art. For example as shown in FIG. 3, the computational complexity for the connection of a the first host application or client 105 to the plurality of hardware devices results in a complexity of (N) (where N is the number of hardware devices 210 associated with the distributed system). Thereafter however, the computational complexity for adding subsequent host applications or clients 105 to the tiered communications architecture is (1), a constant value. Thus for each host application or client 105 added beyond the first, a substantially reduced computational complexity is encountered. Integration of additional host applications 105 therefore requires only a total of M more channels 155 (where M corresponds to the total number of host applications or clients 105 present in the distributed system) to be appropriately connected to the hardware devices 210. The number of channels 155 in the distributed system of the present invention therefore increase as the function (M+N). As a result, the total number of channels 155 required by the distributed system configuration of the present invention grows at a substantially reduced rate and as the complexity of the system increases (i.e. more hosts applications 105 or more hardware devices 210) the computational complexity grows at a slower rate compared to that of conventional distributed systems. This feature of the tiered communications system desirably increases the system scalability and improves management of the distributed system in a manner that will be described in greater detail herein below.

Figure 4:
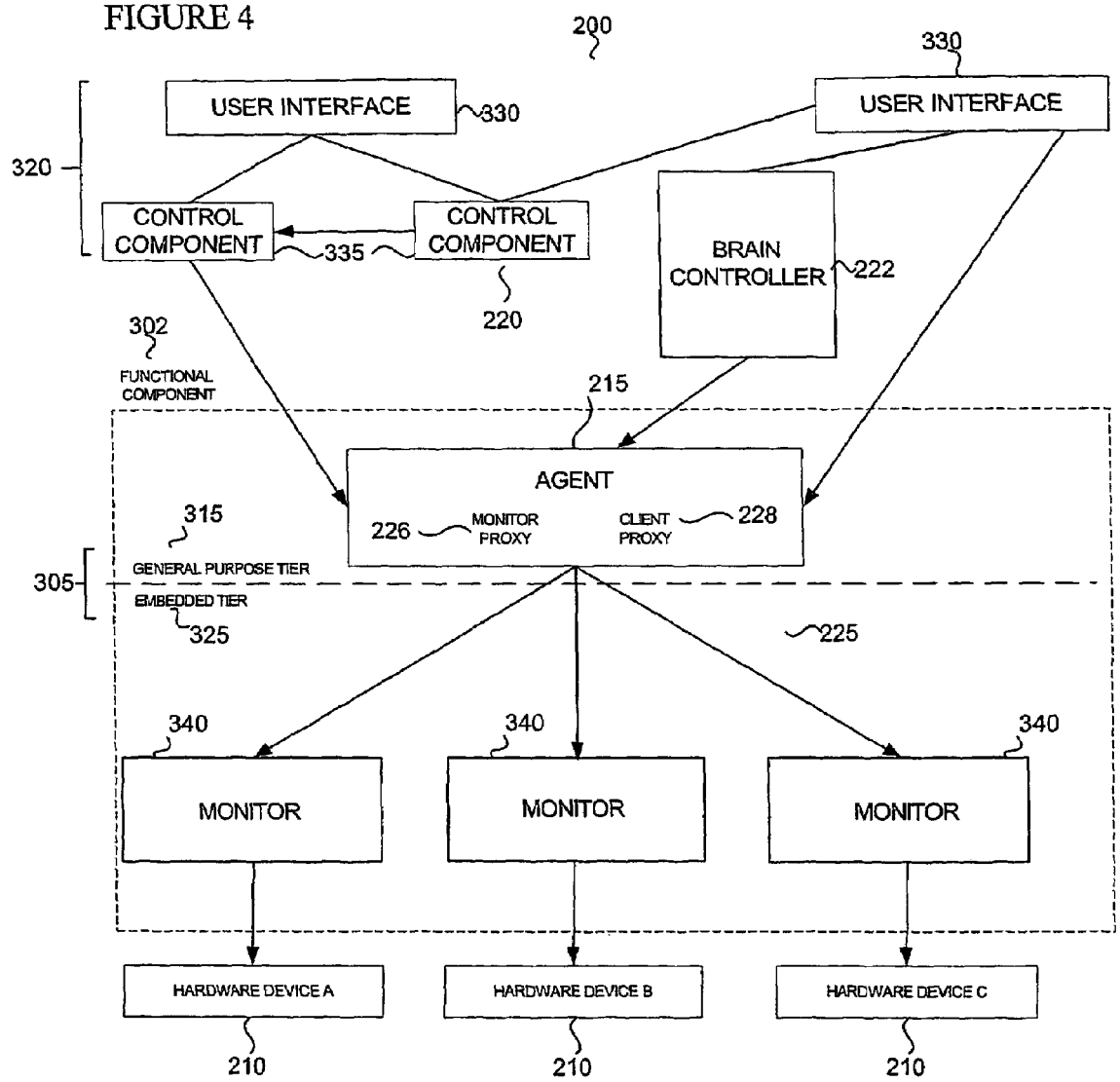
FIG. 4 illustrates one embodiment of a tiered communications system adapted for use with a proton beam therapy device.

FIG. 4 further illustrates the tiered communications architecture 200 adapted for use with the proton beam therapy device 100. Hardware devices 210 which form a particular subsystem, such as the aforementioned beam transport system 170, safety system 175, power system 180, or logging system 185, are desirably associated with a functional component 302. The functional component 302 is subdivided into two logical tiers 305 each of which may also operate on a physical level. The first logical tier comprises a general purpose tier 315 that provides communication interfaces and routing between underlying hardware devices 210 of the functional component 302 and higher level applications or clients 320. Normally, clients 320 send information requests and commands through the general purpose tier 315 in a substantially user-transparent manner. Subsequently, the transmissions are routed to the appropriate hardware devices 210 through a second logical tier comprising an embedded tier 325. Likewise, the underlying hardware devices 210 send information back to the clients 320 in a user transparent manner.

In one aspect the clients 320 comprise control components 335 and user interfaces 330. The control components 335 interact with the functional component 302 and exchange information with the underlying hardware devices 210 to carry out designated control functions. Each control component 335 may further connect to one or more user interfaces 330 to receive input from users and direct information back to the user interface 330 as needed.

In one aspect, one or more control components 335 may interface with other control components 335 to provide a means for direct communication between desired control components 335. Additionally, the control components 335 provide a means for collaboration between a plurality of functional components 302. This collaboration is directed by a one or more specialized controller components referred to as a brain controller 222. Like other control components 220, brain controllers 222 may desirably utilize the services of the functional components 302 directly or indirectly by connecting to other brain controllers 222. Additional details of the brain controller configuration and function will be described in greater detail in connection with FIG. 8.

In another aspect, the user interface 330 can directly interface with the functional component 302 and bypass communication channels through the control components 335 and brain controllers 222. This mode of communication may be used for example, in logging operations, fetching configuration parameters, and data stream applications to transmit information directly between hardware devices 210 of the functional component 302 and the user interface 330.

Agent/General Purpose Tier

The aforementioned agent 215 resides in the general purpose tier 315 of the functional component 302. Each functional component 302 may be associated with an agent 215 that serves as a routing device for messages and information between the client 320 and the underlying hardware devices 210. In one aspect the information transmitted by the client comprises commands, instructions, requests or the like which are desirably issued by the client 320 to monitor and control the hardware devices 210. The agent 215 receives this information from the client 320 and forwards it to one or more monitors 340 which service the communication needs for the underlying hardware devices 210 of the functional component 302. Additionally the agent 215 may be configured to broadcast the desired information to all monitors 340 in the functional component 302 simultaneously depending upon the nature of the information.

The agent 215 further comprises a dual-proxy functionality wherein a monitor proxy functionality 226 is responsible for communications with monitors 340 associated with the functional component 302 and a client proxy functionality 228 is responsible for communications with clients 320. Additionally, the agent 215 manages other network communication functions such as error checking and logging. The agent 215 may further incorporate security features which permit the agent 215 to be configured to recognize "allowed" clients 320 and monitors 240 that are granted access to use the communications facilities of the tiered communications architecture 200.

During routine operation of the distributed system using the tiered communications architecture 200, the system is initialized where the monitor proxy 226 of the agent 215 opens a hardware channel 225 with each available monitor 340. The monitor proxy 226 is a communications proxy that maintains network applications programming interfaces (APIs) that communicate with each monitor 340 in the functional component and is responsible for queuing messages to and from the monitors 340.

Similarly, the client proxy 228 is a communications proxy that maintains network APIs for communicating with clients 320 by opening client channels 220 with each client 320. Unlike conventional systems which require a large number of open channels to allow for communications in the distributed system, in the present invention there is a one to one correspondence between the number of open communications channels 220, 225 and the number of client 320 and hardware devices 210.

In one embodiment, the agent 215 makes use of pointers to message pointer queues wherein the message pointers are passed and the actual messages or information is stored in a shared heap. A first queue is used for messages incoming to the client proxy, a second queue for messages outgoing from the monitor proxy, and a third queue is used for messages incoming to the monitor proxy which are also outgoing to the client proxy (e.g. clean pass-through). Information is transmitted by the agent 215 which initializes a thread that examines messages arriving on the client proxy's incoming queue and places a single message (straight route) or a plurality of messages (broadcast) on the monitor proxy's outgoing queue.

The client proxy maintains a lookup table that maps the addresses of the clients 320 to their network address (i.e. soft IP address). This table is built as messages are received and the entries added to the table are used for routing replies to the messages back to the client 320. Additionally, the agent 215 may maintain configuration data comprising monitor mapping information which is used by the monitor proxy 226 for routing messages to the corresponding destination monitors 340. This information may also be used by the agent 215 to determine which monitors 340 and associated hardware devices 210 are in a particular functional area 302. As a result, a single agent 215 may be configured to coordinate network communications for a plurality of functional components 302 and corresponding hardware devices 210. In one embodiment, the tiered communication architecture 200 is desirably configured to utilize a single agent which coordinates network traffic and messaging for the entire distributed system. The use of the single agent configuration facilitates scaling operations associated with adding new functional components 302 and hardware devices 210 and insures consistency throughout the distributed system.

The agent may further implement various security operations which prevent unauthorized access to the distributed system or selectively block clients 320 which are not recognized for purposes of information transmission at a particular time. One method by which the agent 215 may perform these security operations is to restrict open client channels 200 to only those for clients 320 currently recognized or allowed. It will be appreciated that these security measures may be desirably implemented in the proton beam therapy system to improve patient safety and system security.

Monitor-Proctor/Embedded Tier

The second logical tier comprising the embedded tier 325 provides a network interface or hook that is responsible for translation and communication with the underlying hardware devices 210. The embedded tier 325 for each functional component 302 is desirably substantially user-transparent such that hardware devices 210 of a particular functional component 302 may be accessed and monitored by clients 320 without specific knowledge of their location or address within the distributed system.

The monitors 340 reside at the embedded tier 315 for each functional component 302 and are responsible for exchanging data and information with the agent 215 of the general purpose tier 315. As will be described in greater detail herein below the monitor 340 comprises a plurality of cooperative modules that are responsible for performing functions including information reception, command interpretation and translation, data acquisition, data presentation, and information transmission.

Figure 5:
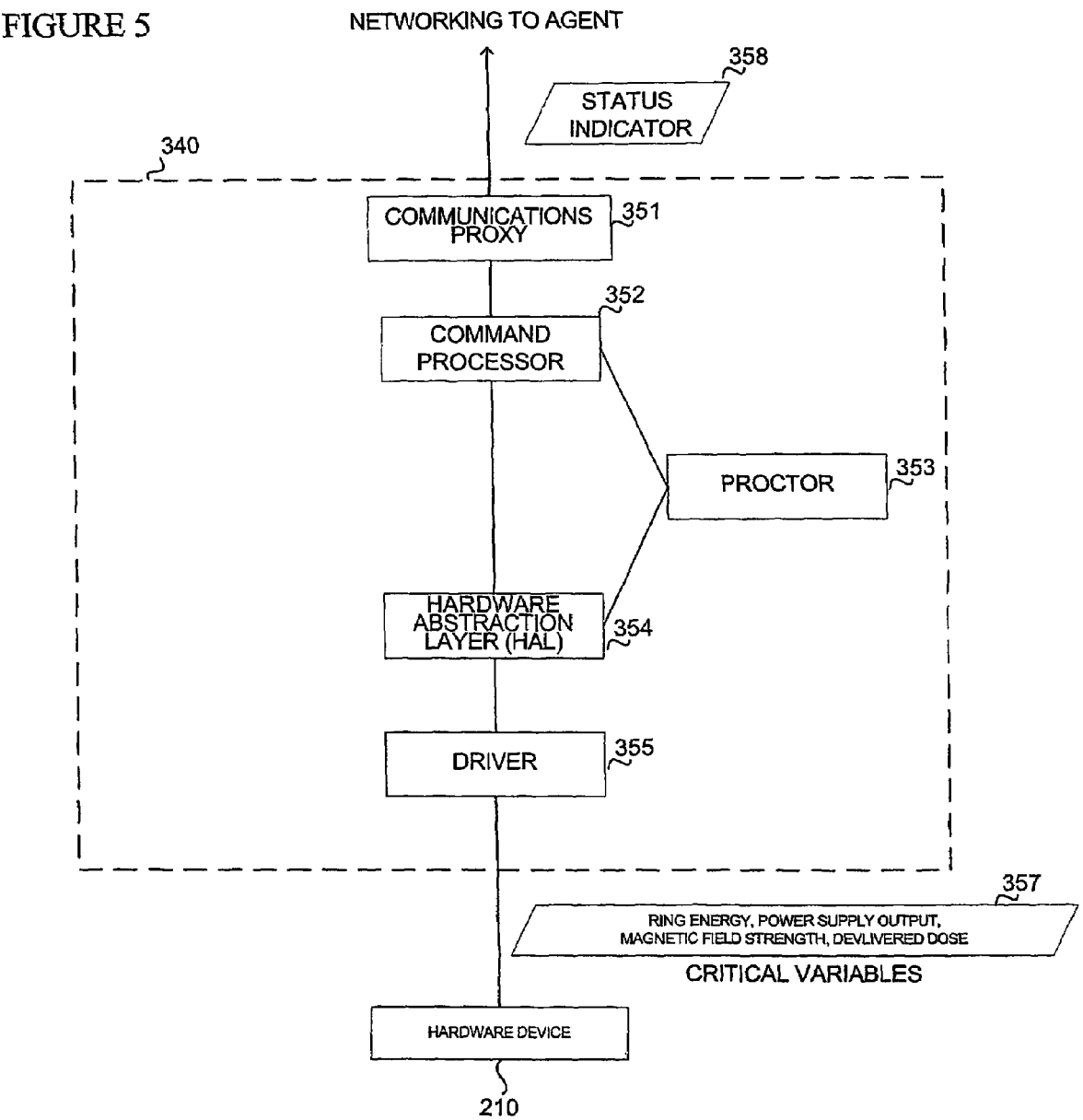
FIG. 5 illustrates one embodiment of a monitor used in connection with the tiered communications system.

FIG. 5 illustrates the cooperative modules of the monitor 340 which reside between the agent 215 and the hardware device 210. The functional components of the monitor 240 include including a proxy 351, a command processor 352, a proctor 353, a hardware abstraction layer 354, and a driver 355. As will be described in greater detail herein below, the activities of these components are desirably coordinated to carry out tasks associated with the processing of information received from clients 320 through the agent 215 and presenting this information to the underlying hardware device 210 in a recognizable form.

The driver 355 resides at the lowest logical level of the monitor 340 and provides hardware interfacing between the functional component 302 and the hardware device 210 with which it interacts. The hardware device 210 may include any of a number of different instruments, devices, apparatuses, or the like which are desirably controlled and monitored by the client 320. Exemplary hardware devices 210 of the proton beam therapy system may include magnets and dosimeters. The driver 351 is responsible for providing an interface to the hardware device 210 so that the desired services of the hardware device 210 can be accessed by the client 320. For each hardware device 210 to be controlled there is at least one driver 351 which interfaces with a portion of the hardware device 210 (i.e. a controller card or the like).

In general, each hardware device 210 recognizes a limited and highly dedicated command set which may include specialized bit/memory addressing or register level commands. These command language definitions and addressing schemes are not typically shared between hardware devices 210 of different classes (e.g. temperature monitors and dosimetry monitors). Additionally, similar hardware devices 210 from different manufacturers may utilize different command structures. Furthermore, the data output and format will typically vary from one hardware device 210 to the next and the data output may be in a format or unit designation which is to be desirably altered for presentation to the client. 320 or other functional components 302. Therefore, in order to communicate with each hardware device 210 a specialized interpreter must be employed.

The driver 351 acts as the specialized interpreter and provides abstraction functions which transform higher level information requests or commands into a native language or code recognized by the hardware device 210. The tiered communication architecture 200 desirably utilizes a "generic" command and information structure when possible to overcome the command language limitations of the hardware devices 210. The generic language codes information in a commonly recognized form across the various components of the tiered communication architecture 200. Information and commands directed towards specific hardware devices 210 are received by the driver 351 which performs the necessary operations to translate the generic code into a hardware recognizable code. Likewise, the driver 351 receives information from the hardware device 210 and translates this information into a generic form which is recognized by other components of the distributed system. The driver 351 may also perform conversion operations such as unit conversions and format transformation to modify the data prior to distribution to the higher level components of the monitor 340.

In one aspect, performing the aforementioned data translation operations at the level of the driver 351 desirably improves system scalability and development flexibility. For example, should an existing hardware device 210 be replaced or upgraded to a different hardware device, minimal modification to the upper level components of the tiered communication architecture 200 is required. Instead the driver 351 may be readily modified to accommodate changes in the syntax or command structure which are used to transform the generic language codes into commands or information that are recognized by the newly installed hardware device. Similarly, the driver 351 may be modified to recognize changes in the format or presentation of data made by the new hardware device without requiring substantive modification of other components of the distributed system. Thus by configuring the tiered communications architecture 200 in this manner improves hardware device transparency and limits the number of changes required to accommodate upgrades and maintenance of the system.

In one aspect, the driver 351 provides a wrapper Application Programming Interface IAPI) to be used to access the underlying hardware device 210. Additionally the driver 351 can be implemented as a collection of thread safe functions which execute as requested by upper-level modules of the monitor 340. The driver 351 typically interfaces with the associated hardware device 210 using memory mapped access to the hardware's registers. Driver interfacing in this manner may utilize a processor contained in the hardware device 210 or a peripheral control card used to control the hardware device 210. This configuration may be referred to as an embedded crate where the crate comprises the hardware device 210, the driver 351, a processor upon which the driver 351 executes and a controller card used by the driver 351 to control the hardware device 210.

In one embodiment driver development and implementation in the embedded crate utilizes an embedded computer operating system and development platform. Using the embedded development platform the driver 351 may be designed to virtualize hardware registers and provides protection and other services required by the hardware device 210. In one aspect, the driver 351 may be configured to present a series of function calls that maintain the logical mapping between the functions and registers within the hardware device 210 and the functions the software developer uses. The functional component 302 may also be configured to make use of the driver 351 to issue function calls to perform actions as needed or requested.

While the driver 351 is focused on hardware device interaction and may provide the interface to the "raw" services of a particular hardware device 210, the hardware abstraction layer (HAL) 354 provides necessary hardware abstraction using the drivers 351 and forms a bridge between the presentation of information by the clients 320 and that of the hardware device 210. The HAL 354 further serves as a translator between the services provided by the distributed system and the hardware device 210 that performs the job. This feature of the HAL 354 significantly reduces problems and difficulties associated with trying to keep each part of the distributed system aware of the current implementation and command structure of each hardware device 210 contained in the functional component 302.

For example, the HAL 354 may receive commands and instructions in engineering units (e.g. Amps, Volts, mTorr, etc) from the clients 320 and translate them into the appropriate driver representations and API calls that are recognized by the underlying hardware devices 210 as acceptable input. Similarly the HAL 354 may receive raw data output and information from the hardware device 210 and perform one or more operations which transform the raw data into a form recognized or desired by the clients 320.

One desirable feature provided by the HAL 354 is the ability to isolate each hardware device 210 used in the distributed system from the command/control functions of the clients 320. More specifically, the HAL 354 is designed to reflect those services required by the clients 320 in a hardware transparent manner and present them to the driver 351 for processing. When hardware devices 210 are changed in the distributed system or if new or different services are requested by the client 320, the HAL desirably requires only minimal modification to accommodate the changes. Furthermore, other components residing above the HAL 354 such as the agent 215 and the clients 320 desirably require little or no modification when changes or additions to the distributed system are made. Instead, the HAL 354 may be updated as needed to accommodate changes in the design of the system by reworking that portion of the code that interfaces the HAL 354 with the driver 351 and the underlying hardware device 210.

The HAL 354 may also provide mechanisms for consolidating a drivers 355 and associated hardware devices 210 into a single meta-device. The meta-device appears logically to the clients 320 as single unit of hardware. Hardware consolidation in this manner desirably reduces the apparent complexity of the system and facilitates monitoring and command of the hardware components of the distributed system. For example, in the proton beam therapy system, a beam scatterer meta-device may be defined as comprising hardware devices 210 including one or more resolvers, a motor controller, digital input, and serial port communications. A single meta-command or instruction issued to the beam scatterer meta-device may thus be used to represent a composite of a plurality of commands and/or instructions that are desirably issued to the various hardware devices 210 of the beam scatterer. The meta-command is recognized by the HAL 354 and the corresponding commands and/or instructions are issued by the HAL 354 through the drivers 351 to the appropriate hardware devices 210. Similarly, the HAL 354 may receive data and information from a plurality of hardware devices 210 contained within the meta-device and perform one or more operations which combine this information and send it back to the client 320 in a consolidated form.

An additional feature of the HAL 354 is that it may be used to internally maintain the mapping of each hardware device 210 within the functional component 302 such that the clients 320 are not required to have knowledge of the specific address or path to the device 210. Instead, the clients 320 may simply direct a command to the monitor 340 which may be subsequently processed and routed to the appropriate hardware device(s) as determined by the HAL 354. It will be appreciated that this feature significantly reduces the mapping complexity in complex distributed systems and provides for improved device transparency. Device transparency is a desirably characteristic as it reduces the apparent complexity of the distributed system and is an aid to developers who are freed from having to discern the actual layout or topology of the hardware devices 210. Additionally, the HAL 354 may be readily redefined to permit modification of the underlying hardware devices 210 or alterations in the composition of devices in the functional component 302 without necessitating substantial reworking of the clients 320.

The monitor 340 further comprises one or more proctors 353 which monitor the performance of the associated hardware devices 210 and acts as handlers for anomalous or undesirable device behavior within the functional components 302. The proctor 353 evaluates the requirements and/or needs of the hardware devices 210 of the functional component 302. Functions performed by the proctor 353 may include monitoring for correct system settings and identifying out of range parameters.

In one aspect, the proctor 353 identifies anomalous device behavior by interpreting data and information received from the hardware device 210. The proctor 353 maintains knowledge of desired tolerances and ranges for hardware devices 210 within the functional component 302 and determines if the hardware devices 210 are performing within desired parameters by comparing actual hardware information with the designated tolerances and ranges. In one aspect, anomalous device behavior in the proton beam therapy system may be identified by evaluating one or more critical variables 357 such as ring energy, power supply output, magnetic field strength, and/or delivered dose. When the value of a critical variable 357 is observed to be outside of the maximum limits or tolerances, the proctor 353 may recognize and report this event. In another aspect, the anomalous behavior may be identified when the critical variable deviates by more than a given limit from a normal value (e.g. a power spike). Additionally, the anomalous behavior may be observed as an adverse trend where the moving average of the deviation is projected by the proctor 353 to be likely out tolerance in a certain time interval.

The proctor 353 may handle anomalous behavior by halting the operation of one or more hardware devices 210 through the issuance of a halt command or instruction. Alternatively, the proctor 353 may permit the hardware device 210 to continue to operate but issue a warning to the client 320 of the anomalous condition. Additionally, the proctor 353 may possess functionality for logging and reporting anomalous behavior to the client 320 in a configurable manner such as by transmission of a status indicator 358.

The proctor 353 further mitigates the drawback of monitoring off-line or malfunctioning systems at the host application level often performed by conventional systems. In one aspect, the proctor features a localized form of hardware device monitoring which may be performed constantly without substantial interaction with the client. In this embodiment, the proctor recognizes a set of conditions or parameters for which the hardware device 110 should desirably operate within. The proctor 353 further monitors the hardware device function and insures that it is operating within these parameters. Should the hardware device 110 deviate from the recognized conditions, the proctor 353 may instruct the monitor to issue appropriate hardware-recognized commands which restore normal operational parameters.

For example, a power supply for the proton beam therapy device 100 may be monitored by the proctor 353 to insure that the output power is consistent with the requested or desired power. Furthermore, the proctor 353 may insure that there are no internal faults within the power supply system. If the proctor 353 for the power supply detects a fault or observes the power supply is not operating within normal parameters, the proctor may generate a report which is transmitted to an outside system thereby giving advance warning of the failure even without a control application or client running. Furthermore, the proctor 353 may take corrective action to restore the power supply to normal operation by instructing the monitor to issue hardware-recognized commands which perform a corrective or restorative function.

In one aspect, the use of the proctor 353 significantly improves patient safety in the particle beam therapy device. By continuously monitoring important hardware devices 210 in an automated manner the proctor 353 can identify dangerous anomalous conditions that are presently occurring and may predict future anomalous conditions that may present a danger to the patient. For example, should the proctor 353 observe that the beam intensity is out of tolerance, the system can be halted preventing potential injury to the patient. Likewise, the proctor 353 may observe that although the beam intensity is currently within acceptable tolerances, an adverse trend may have formed that is used to predict when the beam intensity will be out of tolerance and therefore determine a corrective action should be taken. It will be appreciated that the complexity of the proton beam therapy system is conducive to the automated hardware monitoring and control approach implemented using the proctor 353.

The command processor 352 logically resides directly above the proctor 353 and the HAL 354 both of which are independently connected to this component. The function of the command processor 352 is to interpret and execute incoming instructions received from clients 320. Additionally, the command process provides reply messages in the form of requested data and information received from the hardware device 210.

The command processor 352 performs instruction interpretation by parsing and checking the syntax of incoming instructions or messages and upon verification forwards the instruction to be executed on the appropriate hardware device 210. The forwarded instruction is received by the HAL 354 and as previously mentioned, the HAL 354 performs operations associated with instruction preparation and presentation to the driver 355 for execution on the hardware device 210. Additionally, the command processor 352 forwards the instruction to the proctor 353 which performs operations associated with hardware device monitoring and error detection. Another function of the command processor 352 is to receive data and information from the hardware devices 210 presented by the HAL 354 and proctors 353 and forward this information to the appropriate client(s) 320.

In one aspect, the command processor 352 comprises an information queue that maintains the order of incoming instructions from the clients 320 which are processed in a first in/first out manner. Rather than copying the instructions directly to the queue, the command processor 352 may store pointers to the instructions in order to avoid unnecessary copying of information which may adversely affect system performance when the size of the messages is large. As instructions are processed, the queue is updated accordingly and requested information sent back to the client 320.

The communications proxy 351 logically resides above the command processor 352 and receives incoming data and information from one of more channels associated with the agent 215 and forwards this information directly to the command processor 352. The communications proxy 351 typically does not posses any specialized command or instruction interpreters unlike other components of the monitor 340 but rather is used for information reception and dissemination. Additionally the communication proxy 351 accepts outgoing messages comprising requested information from the command processor 352 and forwards the outgoing message to the appropriate client(s) 320 through the agent 215.

In one aspect, the communications proxy 351 associates instructions received from the clients 320 with the corresponding data or responses sent by the hardware device 210 by maintaining a plurality of network API objects each of which reflect an open channel or socket connection to the monitor 340 from the agent 215. The network API objects are used by the communications proxy 351 to identify the source of the incoming command or instruction so that the results of the instruction can be forwarded to the appropriate client(s) 320 when the results have be received from the command processor 352.

Figure 6:
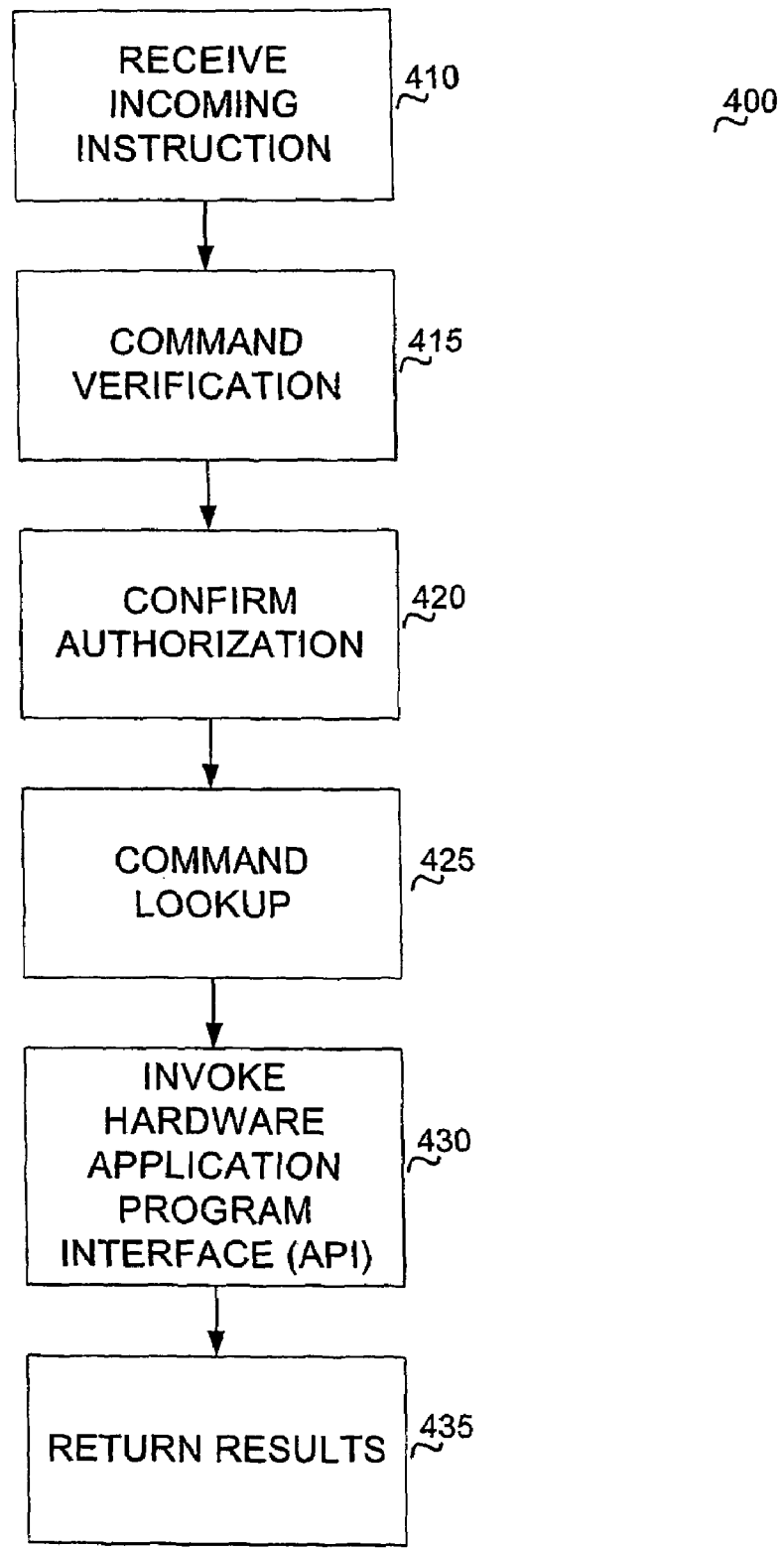
FIG. 6 illustrates a command or instruction process used by the monitor.

FIG. 6 illustrates a process for command or instruction execution using the aforementioned monitor 340. The process commences in a state 410 where an instruction is received from a client 320 that has been forwarded through the agent 215. Command reception is handled by the communications proxy 351 which maintains an open channel with the agent 215. The communications proxy 351 additionally verifies the source of the incoming instruction by identifying the address, channel or IP number from which the instruction originated. This information is used by the communications proxy 351 to identify which client(s) the instruction results should be sent when they are ready.

Proceeding to state 415, the communications proxy 351 forwards the instruction to the command processor 352 for verification. Verification comprises checking the syntax of the instruction to insure that it conforms to a recognized format and possesses the requisite parameters and values which will be distributed to the HAL 354 and proctor 353. Following command verification the process 400 proceeds to a state 420 where the communications proxy 215 performs an authorization check. The authorization check is a validation procedure which confirms that the client 320 requesting access to a particular hardware device 210 or issuing hardware commands actually has permission to do so. In one aspect, the authorization state 420 may be used to implement a level of security in the distributed system by restricting client access to functional components 302 or hardware devices 210. Client access is permitted only when the client 320 is recognized as having sufficient permissions designated by a list stored within the monitor 340. Additionally, the authorization state 420 can be used in blocking procedures to insure that client devices 320 do not access a particular hardware device or resource when that resource is already in use by another client 320 or blocked for other reasons.

Following command verification and authorization the process proceeds to a command lookup state 425 where the command processor 352 determines the correct hardware API and associated hardware device 210 to invoke based upon the input command or instruction. The command processor 352 then sends this information to the appropriate HAL 354 associated with the desired hardware device 210 where the instruction is transformed into a suitable form recognized by the hardware device 210 and executed in state 430.

Results of the hardware invocation are returned in state 435 through the various components of the monitor 340 where they are processed and packaged as described in detail in connection with FIG. 5. Thereafter the communications proxy 351 transmits the results of the command or instruction to the appropriate client(s) 302 thorough the agent 215.

Figure 7:
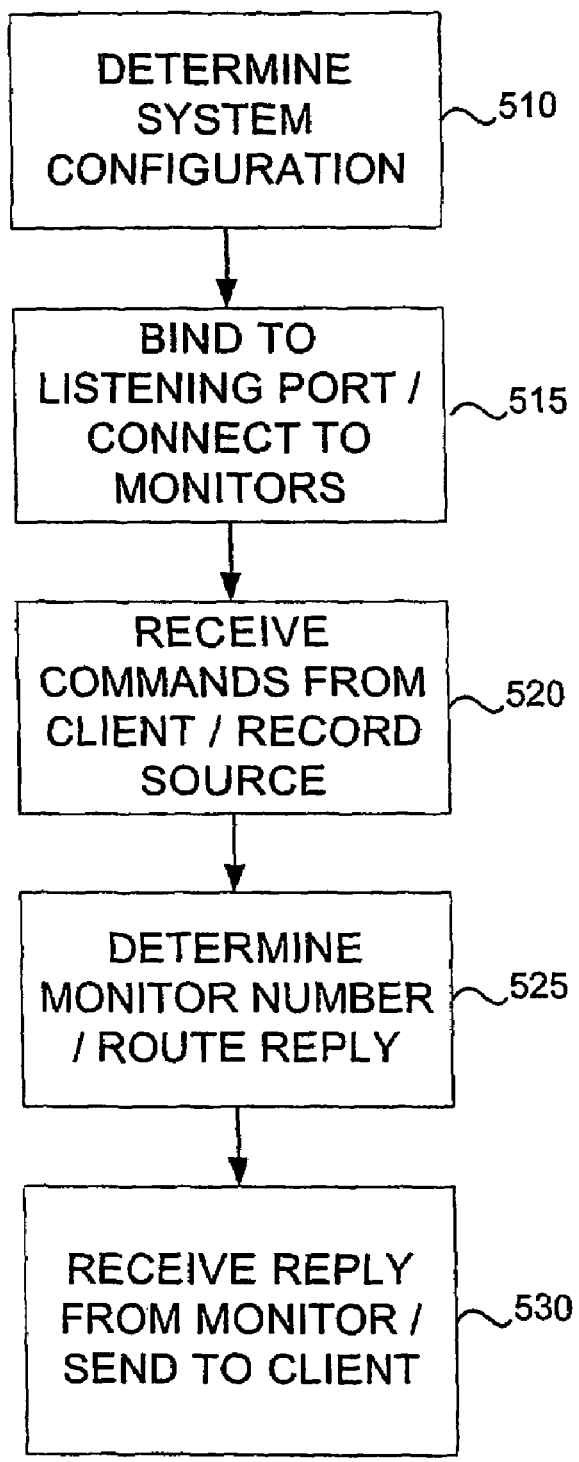
FIG. 7 illustrates an information exchange process used by an agent device in the tiered communications system.

FIG. 7 illustrates an information exchange process using the agent 215 to communicate with the client devices 320 and the monitor 340. The process commences in a state 510 where upon startup of the distributed system, the agent 215 identifies the configuration of the system and the location of the monitor(s) 430 in use for each of the required functional components 302. In one aspect, the configuration of the system is determined by accessing a central configuration file or system which contains channel mapping characteristics to associated crates or hardware devices 210. Additionally, the agent 215 identifies a listening port that defines a dedicated port or channel 155 that will be bound for providing client access. Once this information has been obtained from the central configuration file or system, the agent 215 is bound to the listening port in state 515 and proceeds to establish a connection to each monitor 340 that the agent 215 has been designated to have access.

In state 520, the agent 215 begins normal information processing and communications with the client 320 and monitors 340. When an instruction or information request is received by the agent 215 from a connected client 320, the agent 215 records the source or channel 155 of the request thereby identifying the client 320 from which the instruction originated. Thereafter, in state 525 the agent 215 determines the appropriate monitors 340 which will be sent the instruction. In one aspect, monitors 340 which are designated to receive the instruction are identified using the incoming channel number from which the command originated. Additionally, the source address of the requesting client 215 may be encoded in the data transmission between the client 320 and the agent 215. The source address is resolved by the client 320 to determine the appropriate agent 215 which should receive the results of the instruction. Thereafter, the agent 215 forwards the instruction to the appropriate monitor 340 where the instruction is processed as described in FIG. 6.

When the agent 215 receives a reply containing the results of the instruction from the monitor 340 in state 530, the agent 215 forwards the reply to the appropriate client(s) 320 as determined by the listening port and central configuration file. Thus the agent 215 acts as a intermediary between each client 320 and the hardware associated monitors 340.

Figure 8:
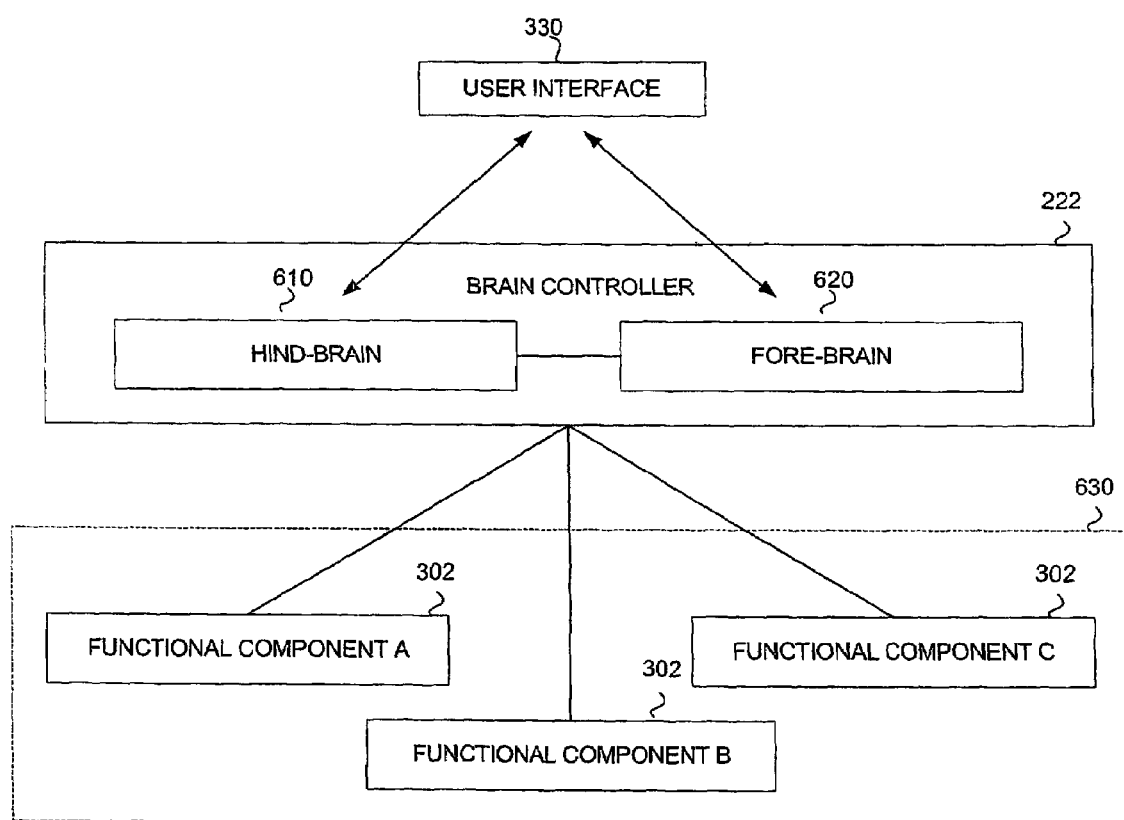
FIG. 8 illustrates one embodiment of a brain controller to be used in connection with the tiered communications system.

FIG. 8 illustrates one embodiment of a brain controller 222 that is used to coordinate command and monitoring activities in the distributed system. The brain controller 222 provides additional computational functionality which is useful in aggregating a plurality of functional components 302 together to form a logical meta-device 630. In one aspect, the meta-device 630 represents a complex functional domain that requires collaboration between the plurality of functional components 302 in order to provide a desired service type.

The brain controller 222 may be further subdivided into a hind-brain 610 and fore-brain 620. The hind brain 610 typically performs operations that do not require extensive decision making or analytical comparisons. For example the hind brain 610 may be used to connect to a plurality of systems or functional components 302 and perform operations such as monitoring and/or operation functions. In one aspect, the hind brain 610 functions autonomously without direct user input from the user interface 330 and interacts directly with one or more functional components 302 through the networking connections or channels 155. The hind brain 610 may be configured to display the status or results of its activities to the user through the user interface 330 however this function is not necessarily required for hind-brain operation. The hind brain 610 may additionally function as an agent for the meta-device 630 which is in turn networked to other agents 215 to provide a means for associating many systems or functional components 302 together.

For example the proton beam therapy system may implement a beam obstruction meta-device which desirably monitors a plurality of separate functional components 302 spread throughout the distributed system, each with their own agent 215. The beam obstruction meta-device may further require knowledge of the treatment mode the particle beam therapy device., is currently in. Additionally, the beam obstruction meta-device may require knowledge of the treatment station 115 which is to receive the proton beam. Using the information obtained from each of these sources the hind brain 610 decides when it is safe to allow the proton beam to be engaged. Because this process involves the coordination of a plurality of functional components 302 spread across the distributed system, a single HAL 354 is typically not suitable to perform operations of this complexity and thus the meta-device may be desirably used to accomplish similar functions.

The fore-brain 620 provides increased analytical functionality compared to the hind-brain 610 and is responsible for implementing complex active control operations. In one aspect, the fore-brain 620 creates operational state machines that ensure the correct steps are taken to perform a particular operation. For example, the fore-brain 620 may be responsible for controlling and monitoring the steps necessary to administer a patient treatment. The fore-brain accomplishes this task by communicating with a plurality of agents 215 and hind-brains 610 sending commands and receiving responses which are used to coordinate the activities of the underlying hardware devices 210. The fore-brain 620 therefore directs the activities of the various subsystems to perform distributed system tasks in a coordinated manner. Additionally, each fore-brain 620 is typically connected to a user interface 330 which is used to interact with the fore-brain 620 directing various system actions and receiving responses or status updates as needed or required.

Although the foregoing description of the invention has shown, described and pointed out novel features of the invention, it will be understood that various omissions, substitutions, and changes in the form of the detail of the apparatus as illustrated, as well as the uses thereof, may be made by those skilled in the art without departing from the spirit of the present invention.

What is claimed is:

1. A communications system for managing communications in a proton beam therapy device, the system comprising:
   a treatment station having a plurality of hardware subsystems used to direct a calibrated and aligned beam towards a patient isocenter;
   one or more host applications used to monitor and control the operation of the treatment station;
   one or more functional components comprising the hardware subsystems associated with the operation of the treatment station wherein the functional component includes one or more proctors that monitors the hardware subsystems wherein the proctor monitors the hardware subsystem independent of the operation of the one or more host applications and implements corrective action without the host applications being active;
   an agent connected to each host application using a single client data channel per host application, the agent further connected to each functional component by a monitor data channel wherein the agent performs routing operations between each host application and the functional components such that each host application can communicate with each functional component using the single client data channel thereby reducing the number of total channels required in the communications system and improving scalability.

2. The communications system of claim 1 wherein each functional component further comprises a monitor which acts as a communications proxy for the functional component and is used to receive communications from the host applications through the agent and transform the communications into instructions that are executed by the hardware subsystems associated with the functional component to calibrate and align the radiation beam.

3. The communications system of claim 2 wherein the monitor further comprises the proctor which assesses the operational parameters of the hardware subsystems, determines if they are within safety tolerances, and performs one or more safety measures if the operational parameters exceed the safety tolerances.

4. The communication system of claim 3, wherein the safety measures performed by the proctor include disabling the hardware subsystems of the functional component to prevent the beam from irradiating the patient isocenter.

5. The communication system of claim 3, wherein the safety measures performed by the proctor include forwarding a status indicator to the host application notifying the host application that the operational parameters of the hardware subsystems have exceeded safety tolerances.

6. The communications system of claim 1 wherein the functional component of the proton beam therapy device comprises a beam transport system used to manage and monitor the redirection of the beam from a beam source to the patient isocenter.

7. The communications system of claim 1 wherein the functional component of the proton beam therapy device comprises a power system used to manage and monitor the power supplied to the treatment station to generate the beam.

8. The communications system of claim 1 wherein the functional component of the proton beam therapy device comprises a logging system used to monitor and log the operational parameters of the proton beam therapy device.

9. The communications system of claim 1 wherein the functional component of the proton beam therapy device comprises a safety system used to monitor the operational parameters of the treatment station and to disengage the beam should the operational parameters exceed a safety threshold.

10. The communications system of claim 1 wherein communication between the host applications and the functional components comprises issuing instructions from the host applications which direct the hardware subsystems of the treatment station and subsequently forwarding operational information back to the host application to allow monitoring of the hardware subsystems.

11. The communications system of claim 10 wherein the agent provides substantially transparent routing of the communications between the host applications and the functional components whereby the host application is not required to be aware of the location of the functional component within the proton beam therapy system.

12. The communications system of claim 10 wherein the agent receives hardware subsystem specific communications from the host application and routes the communications to the appropriate functional component without the requirement that the host application know the address of the functional component within the proton beam therapy system.

13. The communications system of claim 10 wherein the monitor relays information generated by execution of the instructions on the hardware subsystems to the agent which forwards this information back to the host application in a substantially transparent manner.

14. The communications system of claim 1 wherein the agent further incorporates a security function that identifies one or more allowed host applications and routes instructions to the functional component only when the host application is identified as having the appropriate permission to do so.

15. The communication system of claim 1, wherein the host application further comprises a user interface which through which a user inputs the instructions to control or monitor one of more of the plurality of hardware devices and further receives information from one or more of the plurality of hardware devices indicative of their operational status.

16. The communication system of claim 1, wherein the host application comprises a user interface which through which a user inputs the instructions to control or monitor one of more of the plurality of hardware devices and further receives information from one or more of the plurality of hardware devices indicative of the results of the instructions.

17. The communication system of claim 1, wherein the client comprises a brain controller used to coordinate activities of one or more of the hardware devices.

18. The communications system of claim 17, wherein the brain controller comprises a hind-brain component which monitors one or more hardware devices within the proton beam therapy device.

19. The communications system of claim 17, wherein the brain controller comprises a fore-brain component which controls the one or more hardware devices within the proton beam therapy device.

20. The communications system of claim 17, wherein the brain controller is used to aggregate the plurality of hardware devices into a meta-device representative of a coordinated hardware functional domain.

21. The communications system of claim 17, wherein the brain controller operates in an autonomous manner without requiring substantial user input.

22. The communications system of claim 1, wherein the proton beam therapy device comprises a plurality of treatment stations whose functional components are integrated by the agent device such that control and administration of the treatment stations can be centrally coordinated.

23. The communications system of claim 1, wherein the total number of data channels in the communications system grows with a substantially constant complexity as additional clients are integrated into the communications system.

24. The communications system of claim 23, wherein integration of additional host applications and functional components into the proton beam therapy device is facilitated by the substantially constant complexity of growth.

25. A tiered communication architecture for a proton beam therapy device comprising a distributed network which provides substantially transparent communications between one or more host applications and a plurality of hardware devices associated with the generation and alignment of a radiation beam used to treat a patient, the architecture comprising;

an agent device connected to each application and to each hardware device through a plurality of discrete data channels such that a single data channel between the host application and the agent allows communications between the host application and the plurality of hardware devices wherein the agent routes communications between the host application and the plurality of hardware devices through the single data channel thereby reducing the number of data channels required in the distributed network and improving network scalability;

a monitor component associated with each hardware device used to receive instructions from the host application routed through the agent and transform the instructions into a hardware recognized form that are subsequently executed on the hardware device, the monitor component further used to receive an information response from the hardware device and forward the information response back to the host application through agent; and a proctor component resident in the monitor component which evaluates the information response obtained from the hardware device and identifies anomalous hardware behavior and further issues one or more safety measures when anomalous hardware behavior is detected wherein the proctor component monitors the hardware device independent of the operation of the one or more host applications and implements corrective action without the one or more host applications being active.

26. The tiered communication architecture of claim 25 wherein the reduced channel set permits communication between each host application and the plurality of hardware devices by determining the destination hardware device for which a particular instruction issued by the host application is intended and thereafter routes the instruction through the appropriate channel to the destination hardware device without the host application having specific knowledge of where the hardware device is located in the distributed network.

27. The tiered communication architecture of claim 25 wherein the reduced channel set permits communication between the plurality of hardware devices and each host application by determining the host application for which a particular information response issued by the destination hardware device is intended and thereafter routing the information response through the appropriate channel to the host application without the destination hardware device having specific knowledge of where the host application is located in the distributed network.

28. The tiered communication architecture of claim 25 wherein the proctor component identifies anomalous hardware behavior as deviations from desired tolerances or operational ranges for the hardware devices.

29. The tiered communication architecture of claim 25 wherein the anomalous hardware behavior is identified by evaluating a critical variable contained in the information response.

30. The tiered communication architecture of claim 29 wherein the anomalous hardware behavior is identified when the critical variable exceeds a normal value by a maximum tolerance or threshold.

31. The tiered communication architecture of claim 29 wherein the anomalous hardware behavior is identified as an adverse trend where the moving average of the deviation of the critical variable will exceed a normal value in a certain time interval.

32. The tiered communication architecture of claim 29 wherein the critical variable comprises a ring energy variable.

33. The tiered communication architecture of claim 29 wherein the critical variable comprises a power supply output variable.

34. The tiered communication architecture of claim 29 wherein the critical variable comprises a magnetic field strength variable.

35. The tiered communication architecture of claim 29 wherein the critical variable comprises a delivered dose variable.

36. The tiered communication architecture of claim 25 the safety measure issued by the proctor comprises halting the operation one or more of the plurality of hardware devices associated with generating the radiation beam.

37. The tiered communication architecture of claim 25 wherein the safety measure issued by the proctor comprises forwarding a warning to the host application.

38. The tiered communication architecture of claim 25 wherein the safety measure issued by the proctor comprises logging or reporting the anomalous behavior to the host application.

39. The tiered communications system of claim 25, wherein the number of data channels within the distributed network grows with a substantially constant complexity as additional host applications are integrated into the proton beam therapy device.

40. The tiered communications system of claim 39, wherein the substantially constant growth in network complexity in the proton beam therapy device arises as a result of each host application and each hardware device being connected by a single data channel thereby facilitating integration of additional host applications into the proton beam therapy device.

41. The tiered communications system of claim 25, wherein the number of data channels within the distributed network grows with a constant complexity as additional hardware devices are integrated into the proton beam therapy device.

42. The tiered communications system of claim 39, wherein the substantially constant growth in network complexity in the proton beam therapy device arises as a result of each host application and each hardware device being connected by a single data channel thereby facilitating integration of additional hardware devices into the proton beam therapy device.

43. A tiered communications system for managing communications in a distributed network, the system comprising:

a client connected to the distributed network and configured to transmit instructions to a plurality of hardware devices through a single channel, wherein the client and the plurality of hardware devices are part of a proton beam therapy system;

an agent connected to the client through the distributed network and further connected to the plurality of hardware devices such that each hardware device is connected to the agent by a single channel wherein the agent receives the instructions transmitted by the client, identifies a destination hardware device for which the instruction is intended, and routes the instruction to the destination hardware device through an appropriate channel thereby reducing the number of channels required in the distributed network and improving network scalability;

a monitor associated with the destination hardware device and further connected to the distributed network which receives the instruction routed by the agent, identifies a hardware-recognizable command associated with the instruction, and thereafter issues the hardware-recognizable command to the destination hardware device for subsequent execution; and a proctor which monitors the destination hardware device independent of the operation of the client and implements corrective action without the client being activated.

44. The tiered communication system of claim 43, wherein the agent possesses a dual-proxy functionality comprising a monitor proxy used to mediate communications with one or more monitors and a client proxy used to mediate communications with one or more clients such that communications in the distributed network are routed in a substantially transparent manner.

45. The tiered communication system of claim 43, wherein the agent module further incorporates a security function that identifies one or more allowed clients and routes instructions to the destination hardware device only when the client is identified as having the appropriate permission to do so.

46. The tiered communication system of claim 43, wherein the monitor module further comprises:
a communications proxy that receives the instructions routed by the agent;
a command processor that interprets the received instructions by parsing and checking the syntax of the instructions;
the proctor which monitors the performance and operating parameters of the destination hardware device; and
a hardware abstraction layer used to transform the instructions into hardware-recognized commands which are received by the destination hardware device for subsequent execution.

47. The tiered communication system of claim 46, wherein the destination hardware device receives the hardware-recognized commands from the hardware abstraction layer of the monitor, executes the command, and returns operational information corresponding to the executed commands to the monitor for processing by the proctor and forwarding to the client through the agent.

48. The tiered communication system of claim 47, wherein the proctor receives the operational information from the destination hardware device and evaluates its current operation.

49. The tiered communication system of claim 47, wherein the proctor performs one or more safety measures when the current operation of the destination hardware device is determined to be anomalous.

50. The tiered communication system of claim 49, wherein the safety measures include disabling the destination hardware device.

51. The tiered communication system of claim 49, wherein the safety measures include forwarding a status indicator to the client.

52. The tiered communication system of claim 49, wherein the current operation of the destination hardware device is determined to anomalous when the destination hardware device is operating outside of normal operational parameters.

53. The tiered communication system of claim 49, wherein the current operation of the destination hardware device is determined to anomalous when the destination hardware device is malfunctioning or non-operational.

54. The tiered communication system of claim 49, wherein the current operation of the destination hardware device is determined to anomalous when a trend in the current operation of the destination hardware device indicates that it will be operating outside of normal operational parameters at a future time point.

55. The tiered communication system of claim 46, wherein the agent comprises a control component or application used to monitor the operation of at least one of the plurality of hardware devices.

56. The tiered communication system of claim 46, wherein the client comprises a user interface which through which a user inputs the instruction to control or monitor one of more of the plurality of hardware devices and further receives information from one or more of the plurality of hardware devices indicative of their operational status.

57. The tiered communication system of claim 46, wherein the client comprises a user interface which through which a user inputs the instructions to control or monitor one of more of the plurality of hardware devices and further receives information from one or more of the plurality of hardware devices indicative of the results of the instructions.

58. The tiered communication system of claim 46, wherein the client comprises a brain controller used to coordinate activities of one or more of the hardware devices.

59. The tiered communications system of claim 58, wherein the brain controller comprises a hind-brain component which monitors one or more hardware devices within the distributed system.

60. The tiered communications system of claim 58, wherein the brain controller comprises a fore-brain component which controls the one or more hardware devices within the distributed system.

61. The tiered communications system of claim 58, wherein the brain controller is used to aggregate the plurality of hardware devices into a meta-device representative of a coordinated hardware functional domain.

62. The tiered communications system of claim 58, wherein the brain controller operates in an autonomous manner without requiring substantial user input.

63. A method for exchanging information in a proton beam therapy system comprising a client and a plurality of hardware devices wherein the client issues instructions which control and monitor the plurality of hardware devices, the method comprising;
establishing a first communication channel between the client and an agent which is configured to communicate with the client and receive instructions transmitted therefrom;
establishing a plurality of second communication channels between the agent and each hardware device;
routing the instructions issued by the client using the agent such that the instructions are forwarded to the appropriate hardware device in a substantially transparent manner such that the first communication channel between the client and the agent allows client communications with the plurality of hardware devices through the plurality of second communication channels;
receiving the instructions using a monitor module residing on each hardware device which transforms the instructions into a hardware recognized format to be subsequently executed by the hardware device; and
monitoring the hardware devices with a proctor wherein the proctor is independent of the client and implements corrective action without the client being activated.

64. The method for exchanging information of claim 63, wherein the monitor module further receives status information from the hardware device which is subsequently forwarded to the client through the agent.

65. The method for exchanging information of claim 63, wherein the monitor module further includes the proctor which monitors the operation of the hardware devices and determines if the hardware devices are operating within a desired tolerance range.

66. The method for exchanging information of claim 65, wherein the proctor performs one or more safety measures when the hardware devices are determined to be operating outside of the desired tolerance range.

67. The method for exchanging information of claim 66, wherein the safety measures performed by the proctor comprise issuing a status indicator to the client indicative of the current operational function of the hardware device.

68. The method for exchanging information of claim 66, wherein the safety measures performed by the proctor comprise disengaging the hardware device.

69. The method for exchanging information of claim 66, wherein the safety measures performed by the proctor comprise issuing one or more hardware recognized commands which are executed by the hardware device to return it to operation within the desired tolerance range.

70. The method for exchanging information of claim 66, wherein the client and plurality of hardware devices comprise a proton beam therapy system and the exchange of information improves the system's scalability.

71. The method for exchanging information of claim 66, wherein the computational complexity of the system grows as a constant function when new components are added to the proton therapy system.

72. The method for exchanging information of claim 66, wherein the monitor operates in autonomously without receiving instructions from the client.

73. The method for exchanging information of claim 72, wherein autonomous monitor operation is used to monitor off-line devices.

74. The method for exchanging information of claim 72, wherein autonomous monitor operation is used to detect malfunctioning hardware devices and the monitor automatically takes corrective action to return the malfunctioning hardware device to normal operation.

75. The method for exchanging information of claim 72, wherein autonomous monitor operation is used to detect anomalous hardware device behavior and the monitor automatically takes corrective action to return the malfunctioning hardware device to normal operation.

76. The method for exchanging information of claim 72, wherein autonomous monitor operation is used to detect anomalous hardware device behavior and the monitor automatically logs the anomalous behavior for subsequent transmission to the client.

77. A method for exchanging information in a proton beam therapy system comprising one or more host applications and a plurality of hardware devices wherein the host applications are desirably used to control and monitor the plurality of hardware devices through the transmission of a plurality of instructions, the method comprising;
　establishing a first communication channel between each host application and an agent device which is configured to communicate with the host application and receive the transmitted instructions;
　establishing a plurality of second communication channels between the agent device and each hardware device such that each hardware device is connected to the agent by a single communication channel;
　routing the instructions issued by the host applications using the agent device such that the instructions are forwarded to the appropriate hardware device in a substantially transparent manner thereby allowing host application communications with the plurality of hardware devices through the first communication channel substantially reducing the number of communications channels required and improving network scalability;
　receiving the instructions using a monitor module residing on each hardware device which transforms the instructions into a hardware recognized format to be subsequently executed by the hardware device; and
　monitoring the one or more hardware components with one or more proctors that operate independent of the one or more host applications and implement corrective action without the one or more applications being activated.

78. The method for exchanging information in the proton beam therapy system of claim 77, wherein the communication between the host application and the hardware devices is used to monitor one or more critical variables associated with patient treatment.

79. The method for exchanging information in the proton beam therapy system of claim 78, wherein the critical variables are monitored by the proctor to identify anomalous hardware behavior.

80. The method for exchanging information in the proton beam therapy system of claim 79, wherein the anomalous hardware behavior is identified when the critical variable exceeds a normal value by a maximum tolerance or threshold.

81. The method for exchanging information in the proton beam therapy system of claim 79, wherein the anomalous hardware behavior is identified as an adverse trend where the moving average of the deviation of the critical variable will exceed a normal value in a certain time interval.

82. The method for exchanging information in the proton beam therapy system of claim 79, wherein the proctor further halts the operation one or more of the plurality of hardware devices in response to detection of the anomalous hardware behavior.

83. The method for exchanging information in the proton beam therapy system of claim 79, wherein the proctor forwards a warning to the host application in response to detection of the anomalous hardware behavior.

84. The method for exchanging information in the proton beam therapy system of claim 79, wherein the proctor logs or reports the anomalous behavior to the host application.

85. The method for exchanging information in the proton beam therapy system of claim 78, wherein the critical variable comprises a ring energy variable.

86. The method for exchanging information in the proton beam therapy system of claim 78, wherein the critical variable comprises a power supply output variable.

87. The method for exchanging information in the proton beam therapy system of claim 78, wherein the critical variable comprises a magnetic field strength variable.

88. The method for exchanging information in the proton beam therapy system of claim 78, wherein the critical variable comprises a delivered dose variable.

89. A method for communicating and controlling a distributed system of network resources, the method comprising:
　establishing a first communication channel between a client device and an agent device;
　establishing a second communication channel between the agent device and at least one hardware device, wherein the client and at least one hardware device are part of a proton beam therapy system;
　processing data transferred between the client device and the agent device and furthermore the agent device and the monitor device according to a client process which requests access to the distributed system of hardware resources, an agent process which manages the communication channels and provides routing for client process requests, and a monitor process which accepts requests from the agent process, executes the requests, and returns any results to the client process such that client communications through the first communication channel substantially reduces the number of total communications channels required and improving network scalability: and
　monitoring the performance of the at least one hardware device with a proctor wherein the proctor operates independently of the client device and takes corrective action independent of whether the client device is activated.

90. The client process of claim 89, further comprising the steps of:
  receiving the requests from a user through a user interface; and
  transferring the requests from the client device to the agent device.

91. The agent process of claim 89, further comprising the steps of:
  receiving the requests from the client device;
  determining which hardware devices the agent device should forward the requests to; and
  sending the requests to the determined hardware devices.

92. The monitor process of claim 89, further comprising the steps of:
  receiving the requests from the agent device;
  transforming the requests into a hardware recognized instruction that is executed on the hardware device;
  monitoring the status of the hardware device with the proctor to identify anomalous hardware behavior; and
  performing one or more corrective actions when anomalous hardware behavior is detected.

* * * * *